United States Patent
Sullivan et al.

(10) Patent No.: US 9,889,313 B2
(45) Date of Patent: Feb. 13, 2018

(54) EXTERNAL DEFIBRILLATION WITH AUTOMATIC POST-SHOCK ANTI-TACHYCARDIA (APSAT) PACING BASED ON PRE-SHOCK ECG

(71) Applicant: West Affum Holdings Corp., Grand Cayman (KY)

(72) Inventors: Joseph L. Sullivan, Kirkland, WA (US); David Thomas Brown, Lynnwood, WA (US); David Peter Finch, Bothell, WA (US)

(73) Assignee: WEST AFFUM HOLDINGS CORP., Grand Cayman (KY)

( * ) Notice: Subject to any disclaimer, the term of this patent is extended or adjusted under 35 U.S.C. 154(b) by 0 days.

(21) Appl. No.: 15/430,470

(22) Filed: Feb. 11, 2017

(65) Prior Publication Data

US 2017/0151441 A1 Jun. 1, 2017

Related U.S. Application Data

(62) Division of application No. 13/802,399, filed on Mar. 13, 2013, now Pat. No. 9,604,070.

(Continued)

(51) Int. Cl.
*A61N 1/39* (2006.01)
*A61N 1/362* (2006.01)

(52) U.S. Cl.
CPC .......... *A61N 1/3987* (2013.01); *A61N 1/3621* (2013.01); *A61N 1/3625* (2013.01); *A61N 1/3925* (2013.01); *A61N 1/3993* (2013.01)

(58) Field of Classification Search
CPC .. A61N 1/3962; A61N 1/3925; A61N 1/3987; A61N 1/3621; A61N 1/3625
(Continued)

(56) References Cited

U.S. PATENT DOCUMENTS 3,724,355 A  4/1973 Unger
4,583,524 A  4/1986 Hutchins
(Continued)

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.
(Continued)

*Primary Examiner* — Michael Carey
(74) *Attorney, Agent, or Firm* — Kavounas Patent Law Office, PLLC

(57) ABSTRACT

A medical device such as an external defibrillator delivers electrical therapy using a special pulse sequence. The special pulse sequence includes a defibrillation shock that is automatically followed by a quick succession of automatic post-shock anti-tachycardia (APSAT) pacing pulses. Because of the pacing pulses, the defibrillation shock can be of lesser energy than an equivalent defibrillation shock of a larger energy. Accordingly, the external defibrillator can be made physically smaller and weigh less, without sacrificing the therapeutic effect of a larger external defibrillator that would deliver a defibrillation shock of higher energy. As such, the defibrillator is easier to configure for transporting, handling, and even wearing.

21 Claims, 5 Drawing Sheets

DEFIBRILLATION SCENE

Related U.S. Application Data

(60) Provisional application No. 61/711,845, filed on Oct. 10, 2012.

(58) Field of Classification Search
USPC .................................................. 607/4, 5, 7, 8
See application file for complete search history.

(56) References Cited

U.S. PATENT DOCUMENTS

| | | | |
|---|---|---|---|
| 4,619,265 A | 10/1986 | Morgan et al. | |
| 5,228,449 A | 7/1993 | Christ et al. | |
| 5,353,793 A | 10/1994 | Bomn | |
| RE34,800 E | 11/1994 | Hutchins | |
| 5,394,892 A | 3/1995 | Kenny | |
| 5,405,362 A | 4/1995 | Kramer et al. | |
| 5,662,690 A | 9/1997 | Cole et al. | |
| 5,782,878 A | 7/1998 | Morgan et al. | |
| 5,792,204 A | 8/1998 | Snell | |
| 5,902,249 A | 5/1999 | Lyster | |
| 5,913,685 A | 6/1999 | Hutchins | |
| 6,047,203 A | 4/2000 | Sackner et al. | |
| 6,065,154 A | 5/2000 | Hulings et al. | |
| 6,108,197 A | 8/2000 | Janik | |
| 6,201,992 B1 | 3/2001 | Freeman | |
| 6,246,907 B1 * | 6/2001 | Lin | A61B 5/0456 600/518 |
| 6,263,238 B1 | 7/2001 | Brewer et al. | |
| 6,287,328 B1 | 9/2001 | Snyder et al. | |
| 6,319,011 B1 | 11/2001 | Motti et al. | |
| 6,334,070 B1 | 12/2001 | Nova et al. | |
| 6,356,785 B1 | 3/2002 | Snyder | |
| 6,529,875 B1 | 3/2003 | Nakajima | |
| 6,980,856 B2 | 12/2005 | Sullivan et al. | |
| 7,559,902 B2 | 7/2009 | Ting et al. | |
| 7,565,194 B2 * | 7/2009 | Tan | A61B 5/0464 600/509 |
| 7,865,238 B2 | 1/2011 | Brink | |
| 7,870,761 B2 | 1/2011 | Valentine | |
| 8,644,925 B2 | 2/2014 | Volpe et al. | |
| 8,897,860 B2 | 11/2014 | Volpe et al. | |
| 8,965,500 B2 | 2/2015 | Macho et al. | |
| 9,131,901 B2 | 9/2015 | Volpe et al. | |
| 9,132,267 B2 | 9/2015 | Kaib | |
| 2001/0027330 A1 * | 10/2001 | Sullivan | A61N 1/39 607/4 |
| 2003/0060723 A1 | 3/2003 | Joo et al. | |
| 2003/0158593 A1 | 8/2003 | Heilman et al. | |
| 2004/0215239 A1 * | 10/2004 | Favet | A61N 1/3622 607/4 |
| 2005/0107833 A1 | 5/2005 | Freeman et al. | |
| 2005/0107834 A1 | 5/2005 | Freeman et al. | |
| 2011/0288605 A1 | 11/2011 | Kaib et al. | |
| 2012/0144551 A1 | 6/2012 | Guldalian | |
| 2012/0158075 A1 | 6/2012 | Kaib et al. | |
| 2012/0265265 A1 | 10/2012 | Razavi et al. | |
| 2013/0317852 A1 | 11/2013 | Worrell et al. | |
| 2014/0378812 A1 | 12/2014 | Saroka et al. | |

OTHER PUBLICATIONS

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

* cited by examiner

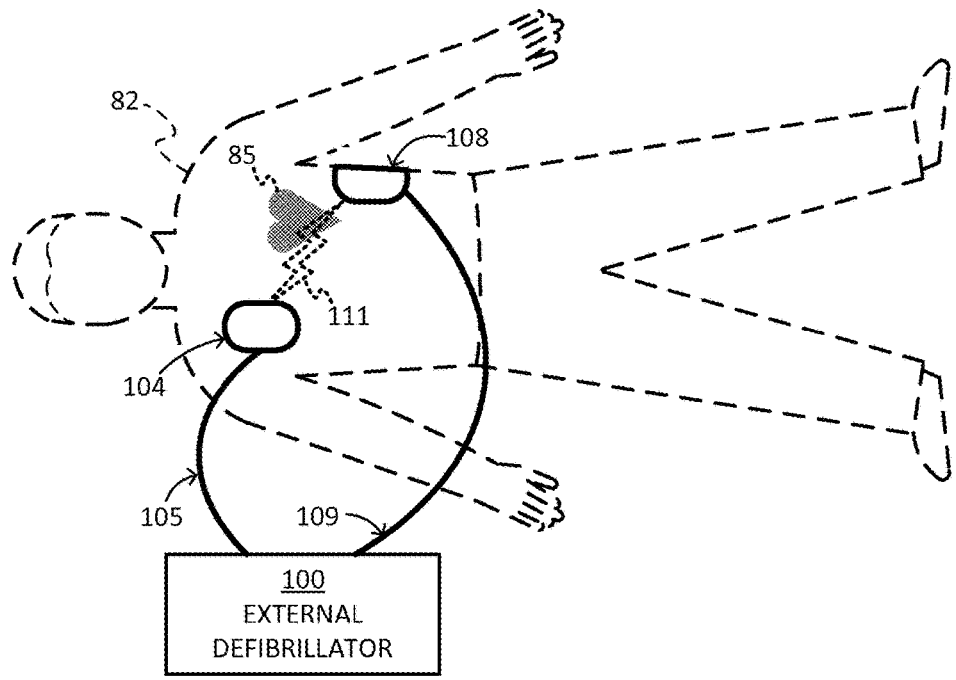
FIG. 1  *DEFIBRILLATION SCENE*
| TYPE OF EXTERNAL DEFIBRILLATOR | INTENDED TO BE USED BY PERSONS: | |
|---|---|---|
| | IN THE MEDICAL PROFESSIONS | NOT IN THE MEDICAL PROFESSIONS |
| DEFIBRILLATOR – MONITOR | √ | |
| AED | √ | √ |
FIG. 2  *EXAMPLES OF EXTERNAL DEFIBRILLATORS*

*COMPONENTS OF EXTERNAL DEFIBRILLATOR*

*EXTERNAL DEFIBRILLATION WITH APSAT PACING*

FIG. 5 METHODS

EXTERNAL DEFIBRILLATION WITH AUTOMATIC POST-SHOCK ANTI-TACHYCARDIA (APSAT) PACING BASED ON PRE-SHOCK ECG

CROSS REFERENCE TO RELATED PATENT APPLICATIONS

This patent application is a divisional of U.S. patent application Ser. No. 13/802,399, filed on Mar. 13, 2013, which was issued as No. U.S. Pat. No. 9,604,070 B2 on Mar. 28, 2017, and which in turn claims priority from U.S. Provisional Patent Application Ser. No. 61/711,845, filed on Oct. 10, 2012, the disclosure of which is hereby incorporated by reference for all purposes.

BACKGROUND

In humans, the heart beats to sustain life. In normal operation, the heart pumps blood through the various parts of the body. In particular, the various chambers of the heart contract and expand periodically, and coordinated so as to pump the blood regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle then expels the blood, forcing it to circulate to the various parts of the body.

The heart chambers pump because of the heart's electrical control system. In particular, the sinoatrial (SA) node generates an electrical impulse, which generates further electrical signals. These further signals cause the above-described contractions of the various chambers in the heart to take place in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In a SCA, the heart fails to pump blood effectively, and, if not treated, death can occur. In fact, it is estimated that SCA results in more than 250,000 deaths per year in the United States alone. Further, a SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not reversed in time, they will die soon, e.g. within ten minutes.

Ventricular Fibrillation can often be reversed using a life-saving device called a defibrillator. A defibrillator, if applied properly, can administer an electrical shock to the heart. The shock may terminate the VF, thus giving the heart the opportunity to resume pumping blood. If VF is not terminated, the shock may be repeated, sometimes at escalating energies.

A challenge with defibrillation is that the electrical shock must be administered very soon after the onset of VF. There is not much time: the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. To-date, for some people who are considered to be at a higher risk of VF or other heart arrythmias, an Implantable Cardioverter Defibrillator (ICD) is implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at a high risk. Cardiac events can be experienced by people who lack the benefit of ICD therapy. When VF occurs to a person who does not have an ICD, they collapse, because blood flow has stopped. They should receive therapy quickly.

For a VF victim without an ICD, a different type of defibrillator can be used, which is called an external defibrillator. External defibrillators have been made portable, so they can be brought to a potential VF victim quickly enough to revive them. The time from the collapse to the time a portable defibrillator is applied to the cardiac event victim is critical. Often, a physician can perceive and determine that a patient is at a risk that would qualify the patient for the invasive ICD implant. In such cases, a wearable defibrillator/monitoring device would be highly desirable.

During VF, the person's condition deteriorates, because the blood is not flowing to the brain, heart, lungs, and other organs, which can be damaged as a result. Accordingly, defibrillation must be applied quickly, to restore the blood flow. To expedite defibrillation, there have been efforts to make defibrillators ubiquitous, portable and, when needed, wearable by a prospective patient. All these efforts can be facilitated by making an external defibrillator smaller and weigh less. A persisting need exists for a smaller, lighter, and more portable defibrillator without compromising therapy and/or monitoring efficacy.

BRIEF SUMMARY

The present description gives instances of medical devices, processors, and methods, the use of which may help overcome problems and limitations of the prior art.

In one embodiment, an external defibrillator delivers electrical therapy using a special pulse sequence. The special pulse sequence includes a defibrillation shock that is automatically followed by a quick succession of automatic post-shock anti-tachycardia (APSAT) pacing pulses. Because of the pacing pulses, the defibrillation shock can be of lesser energy than an equivalent defibrillation shock of a higher energy. Accordingly, an external defibrillator can be made according to embodiments of the invention physically smaller and weigh less, without sacrificing the therapeutic effect of a larger external defibrillator that would deliver a higher energy defibrillation shock. As such, a defibrillator made according to embodiments of the invention is easier to configure for transporting, handling, and, when desirable, wearing.

These and other features and advantages of this description will become more readily apparent from the following Detailed Description, which proceeds with reference to the drawings, in which:

BRIEF DESCRIPTION OF THE DRAWINGS

FIG. 1 is a diagram of a scene where an external defibrillator is used to save the life of a person according to embodiments.

FIG. 2 is a table listing examples of types of the external defibrillator shown in FIG. 1, and who they might be used by.

DETAILED DESCRIPTION

Figure 3:
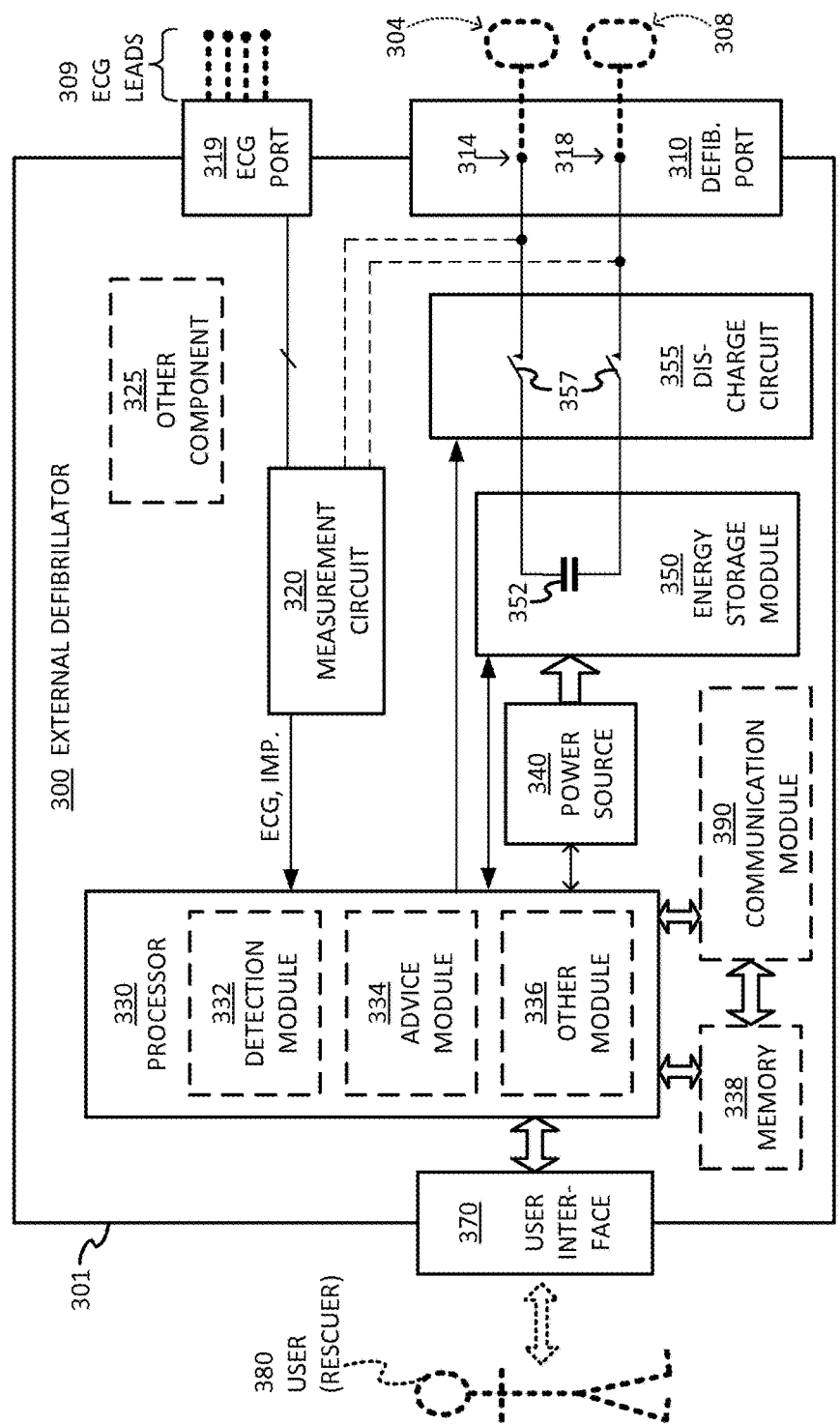
FIG. 3 is a diagram showing components of an external defibrillator, such as the one shown in FIG. 1, which is made according to embodiments.

As has been mentioned, the present description is about external defibrillators, processors, and methods of delivering electrical therapy using a special pulse sequence. Embodiments are now described in more detail.

Defibrillation Scene

FIG. 1 is a diagram of a defibrillation scene. A portable external defibrillator 100 is being applied to a person 82. Person 82 could be experiencing a condition in their heart 85, which could be Ventricular Fibrillation (VF) or a different arrhythmia. The scene of FIG. 1 could be in a hospital, where person 82 is a patient, or in some other location where an SCA victim is unconscious and then turned to be on their back. Alternatively, person 82 could be someone who is wearing defibrillator 100.

Defibrillator 100 is usually provided with at least two defibrillation electrodes 104, 108, which are sometimes called just electrodes 104, 108. Electrodes 104, 108 are coupled with external defibrillator 100 via respective electrode leads 105, 109. A rescuer (not shown) has attached electrodes 104, 108 to the skin of person 82. Alternatively, if defibrillator 100 is wearable, electrodes 104, 108 have been applied to the skin before the event, or automatically.

Defibrillator 100 is configured to administer electrical therapy 111 to person 82. In other words, defibrillator 100 can cause, via electrodes 104, 108, electrical energy to go through the body of person 82, in an attempt to affect heart 85. Therapy 111 can include a brief, strong defibrillation pulse, which is also known as a defibrillation shock, in an attempt to restart heart 85 so as to save the life of person 82.

Defibrillator 100 can be one of different types, each with different sets of features and capabilities. The set of capabilities of defibrillator 100 is determined by planning who would use it, and what training they would be likely to have. Examples are now described.

Types of External Defibrillators

FIG. 2 is a table listing examples of types of external defibrillators, and who they are primarily intended to be used by. One of defibrillator 100 is generally called a defibrillator-monitor, because it is typically formed as a single unit in combination with a patient monitor. A defibrillator-monitor is sometimes called monitor-defibrillator. A defibrillator-monitor is intended to be used by persons in the medical professions, such as doctors, nurses, paramedics, emergency medical technicians, etc. Such a defibrillator-monitor is typically intended to be used in a pre-hospital or hospital scenario.

As a defibrillator, the device can be one of different varieties, or even versatile enough to be able to switch among different modes that individually correspond to the varieties. One variety is that of an automated defibrillator, which can determine whether a shock is needed and, if so, charge to a predetermined energy level and instruct the user to administer the shock. Another variety is that of a manual defibrillator, where the user determines the need and controls administering of the shock.

As a patient monitor, the device has features additional to what is minimally needed for mere operation as a defibrillator. These features can be for monitoring physiological indicators and other data of a person in an emergency scenario. These physiological indicators and other data are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

Another type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a simpler construction, an AED typically costs much less than a defibrillator-monitor. As such, it makes sense for a hospital, for example, to, as a back-up, deploy AEDs at its various floors, in case the more expensive defibrillator-monitor is more critically being deployed at an Intensive Care Unit, and so on.

AEDs can also be used by people who are not in the medical professions. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Indeed, the people who will first reach the VF sufferer may not be in the medical professions.

Increasing awareness has resulted in AEDs being deployed in public or semi-public spaces, so that even a member of the public can use one, if they have obtained first aid and CPR/AED training on their own initiative. This way, defibrillation can be administered soon enough after the onset of VF, to hopefully be effective in rescuing the person.

With either of the described-above types of defibrillator, a cardiac victim must depend on prompt responsiveness of a bystander/rescuer. Another type of such a defibrillator is a wearable defibrillator, which is configured so that it can be worn by the patient for long time durations. These time durations are preferably days and weeks, and in any event at least one hour. Wearable defibrillator is capable of automatic autonomous response to a cardiac event. The delay from the onset of the event to the administration of therapy/care is in this case dramatically reduced. There are additional types of external defibrillators, which are not listed in FIG. 2. For example, a hybrid defibrillator can have aspects of an AED, and also of a defibrillator-monitor. A usual such aspect is additional ECG monitoring capability. Other types of defibrillators are possible, as would be apparent to a person skilled in the art.

Example External Defibrillator

FIG. 3 is a diagram showing components of an example external defibrillator 300 made according to embodiments. These components can be, for example, in external defibrillator 100 of FIG. 1. Plus, these components of FIG. 3 can be provided in a housing 301, which is also known as casing 301 or may work as a system 301 comprised of modular components interacting with one another.

External defibrillator 300 is intended for use by a user 380, who would be the rescuer. Defibrillator 300 typically includes a defibrillation port 310, such as a socket in housing 301. Defibrillation port 310 includes nodes 314, 318. Defibrillation electrodes 304, 308, which can be similar to electrodes 104, 108, can be plugged in defibrillation port 310, so as to make electrical contact with nodes 314, 318, respectively. It is also possible that electrodes can be connected continuously to defibrillation port 310, etc. Either way, defibrillation port 310 can be used for guiding via electrodes to person 82 an electrical charge that has been stored in defibrillator 300, as will be seen later in this document.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or from a different number of leads. Moreover, a defibrillator-monitor could have additional ports (not shown), and another component 325 for the above described additional features, such as patient signals.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 is an article that may be implemented in any number of ways. Such ways include, by way of example and not of limitation, digital and/or analog processors such as microprocessors and digital-signal processors (DSPs); controllers such as microcontrollers; software running in a machine or a chip; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 can be considered to have a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at advice based on outputs of detection module 332. Advice module 334 can include a Shock Advisory Algorithm, implement decision rules, and so on. The advice can be to shock, to not shock, to administer other forms of therapy, and so on. If the advice is to shock, some external defibrillator embodiments merely report that to the user, and prompt them to do it. Other embodiments further execute the advice, by administering the shock. If the advice is to administer CPR, defibrillator 300 may further issue prompts for it, and so on.

Processor 330 can include additional modules, such as module 336, for other functions. In addition, if other component 325 is indeed provided, it may be operated by or included in processor 330, in whole or in part, etc.

Defibrillator 300 optionally further includes a memory 338, which can work together with processor 330. Memory 338 may be implemented in any number of ways. Such ways include, by way of example and not of limitation, nonvolatile memories (NVM), read-only memories (ROM), random access memories (RAM), any combination of these, and so on. Memory 338, if provided, can include programs for processor 330, and so on. The programs can be operational for the inherent needs of processor 330, and can also include protocols and ways that decisions can be made by advice module 334. In addition, memory 338 can store prompts for user 380, acquired or entered data about patient 82, etc.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include AC power override, for where AC power will be available, and so on. In some embodiments, power source 340 is controlled by processor 330.

Defibrillator 300 additionally includes an energy storage module 350. Module 350 is where some electrical energy can be stored, when it is being prepared for sudden discharge to administer one or more electrical discharges, as will be described later in this document. Module 350 can be charged from power source 340 to the right amount of energy, as controlled by processor 330. In typical implementations, module 350 includes one or more capacitors 352, and so on. Energy storage module 350 typically becomes recharged, after it delivers energy. Opportune times for such recharging are after delivering the defibrillation shock 448 described below, whether before, in-between, or after the pacing pulses that follow. More aggressive recharging may be needed depending on the desired ATP pulse level and the patient's bulk impedance.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and so on.

Defibrillator 300 further includes a user interface 370 for user 380. User interface 370 can be made in any number of ways. For example, interface 370 may include a screen, to display what is detected and measured, provide visual feedback to the rescuer about their resuscitation attempts, and so on. Interface 370 may also be able to issue audible prompts, such as by having a speaker for voice prompts, etc. Interface 370 may additionally include various controls, such as pushbuttons, keyboards, touchscreens, and so on. In addition, discharge circuit 355 can be controlled by processor 330, or directly by user 380 via user interface 370, and so on.

Defibrillator 300 can optionally include other components. For example, a communication module 390 may be provided for communicating with other machines. Such communication can be performed wirelessly, or via wire, or by infrared communication, and so on. This way, data can be communicated, such as patient data, incident information, therapy attempted, CPR performance, and so on.

As mentioned above, defibrillator 300 is capable of delivering therapy using a special pulse sequence. More particularly, processor 330 may determine whether defibrillation is advised for the patient, for example by using advice module 334. If defibrillation is indeed advised, processor 330 may control delivery of the energy stored in energy storage module 350. The therapy is in the form of a special pulse sequence, as is now described in more detail.

Example Timing Diagrams

Figure 4:
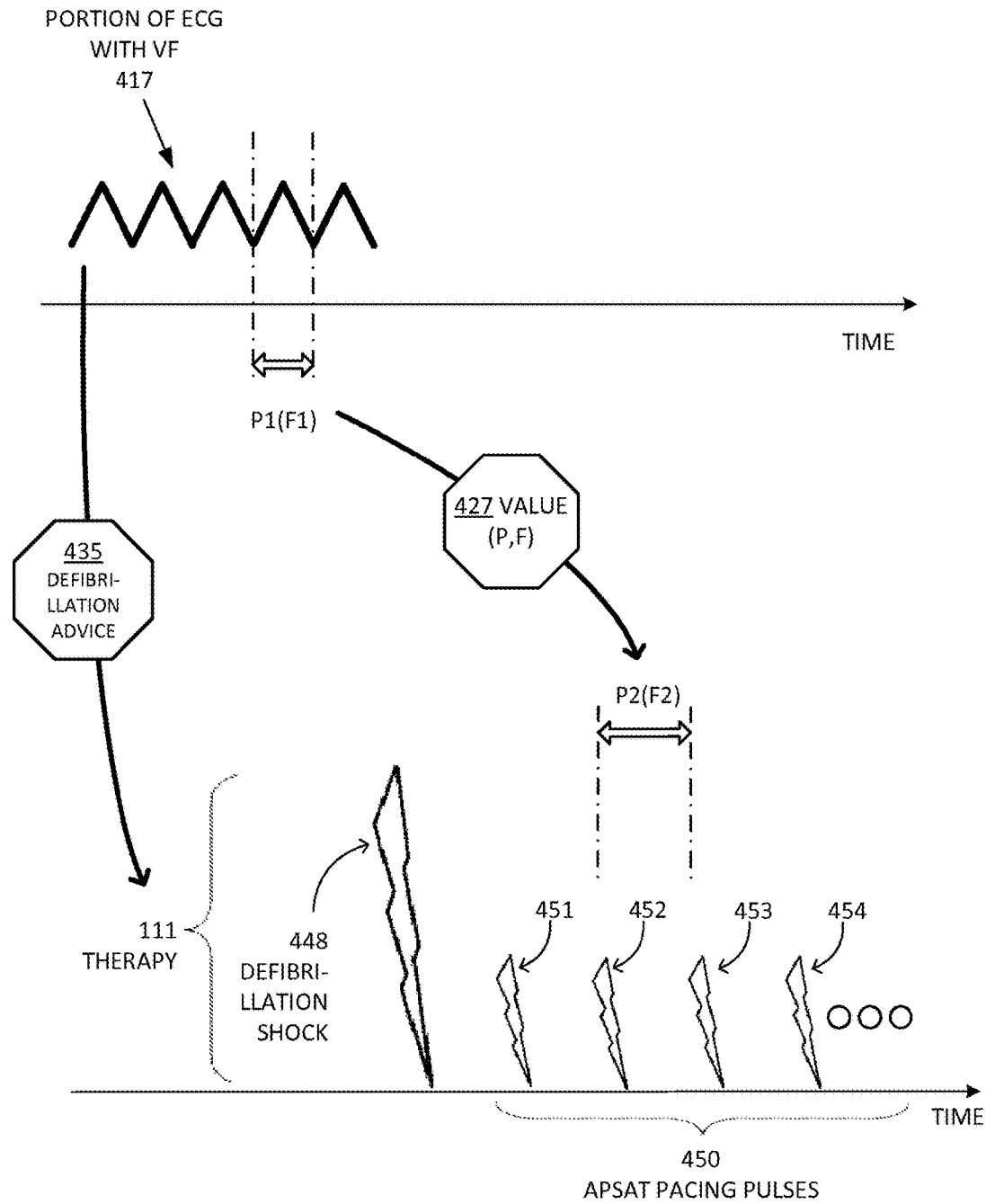
FIG. 4 is a combination of timing diagrams for illustrating the timing of a pulse sequence according to embodiments.

FIG. 4 is a combination of example timing diagrams for illustrating the timing of a pulse sequence according to embodiments. Therapy 111 is shown along a time axis, in terms of icons that represent delivery of energy to the patient as therapy. It will be understood that, in some embodiments, the energy of therapy 111 is delivered automatically, in response to determining that defibrillation is advised for the patient. In other embodiments, the energy is delivered responsive to a user operating the user interface 370; in those embodiments, the user would be informed that defibrillation is advised, or to activate a control, or both. In some embodiments, the energy delivered as therapy is delivered in different portions. Often a first portion is a defibrillation shock, and often a second portion is one or more pacing pulses, as described in more detail below.

Therapy 111 includes energy delivered as a defibrillation shock 448. Defibrillation shock 448 can be delivered in any way known in the art. For example, shock 448 could be a monophasic shock, a biphasic shock, or other multiphasic shock. Shock 448 could be delivered by only two electrodes, or it could be a multi-vector shock, such as from multiple electrodes or segmented electrodes with different active segments.

Defibrillation shock 448 is clearly distinguishable from, say, pacing pulses. For example, in many embodiments, defibrillation shock 448 has energy of at least 50 Joules (J) for an adult. The defibrillation energy can be smaller, if the patient is a child or an infant.

Therapy 111 also includes energy delivered as a group 450 of APSAT pacing pulses 451, 452, 453, 454, . . . , shortly after defibrillation shock 448. Pulse 451 is also called a lead pacing pulse 451. The pacing pulses of group 450 are clearly distinguishable from a defibrillation pulse—for example they have energy of less than 5 J, or often less than 3 J. For example, a 200 mA pacing pulse, 40 ms long, into a 100 ohm load, delivers ~0.16 J; and into a 2K ohm load, 3.2 J.

For purposes of this document, "APSAT" stands for "Automatic Post-Shock Anti-Tachycardia", to connote the pulses of group 450. In some embodiments, the pulses of group 450 are automatic, in that lead pacing pulse 451 is delivered without analyzing an ECG of the patient in a time interval between when defibrillation shock 448 has been delivered and lead pacing pulse 451 has been delivered, and/or without making any other preparation or needing to receive any input for lead pacing pulse 451 after defibrillation shock 448 has been delivered. The automatic aspect can be extended to others of the pacing pulses, such as 452, 453, 454, etc.; in other words, two or more of the pacing pulses of group 450 can be delivered as part of a single prepared stack that includes shock 448, without analyzing an ECG of the patient while the stack is being delivered. An advantage is that there will be no need, in some embodiments, for a separate set of electrodes to input the ECG.

In some embodiments, lead pacing pulse 451 occurs within five seconds after defibrillation shock 448 has been delivered. Often the time is shorter than five seconds—in fact the whole therapy 111 may be completed within less than five seconds. An advantage is that there will be no need to assess whether the patient is conscious and, if so, to sedate them. In fact, VF patients tend not achieve consciousness very quickly after defibrillation shock 448. Accordingly, there is no need to sedate the patient, and the pacing pulses 451, . . . can be delivered at a level known to capture (e.g. 200 mA) without regard for pain.

In some embodiments, processor 330 is configured to determine whether defibrillation is advised for the patient by performing an analysis of an ECG of the patient. For example, the ECG may indicate that the patient has VF or Ventricular Tachycardia ("VT"). In some of these embodiments, the energy of therapy 111 is ultimately delivered via electrodes, and the ECG is received from the patient via the same electrodes. An example is now described.

In FIG. 4, a portion 417 of an ECG waveform is shown against a time axis. Portion 417 has VF, which generates defibrillation advice 435 that therapy 111 is advised.

In addition, an inter-pulse time duration is determined from the analysis of the ECG. The inter-pulse time duration can be advantageously determined by processor 330, although that is not necessary for practicing embodiments of the invention.

The inter-pulse time duration can be used for the spacing of the pacing pulses in group 450. In one embodiment, two successive ones of the pacing pulses can have that spacing between them. For example, in FIG. 4, pacing pulses 452, 453 are successive, and pacing pulse 453 is delivered the inter-pulse time duration P2 after pacing pulse 452.

The inter-pulse time duration P2 may be known also by its inverse, frequency F2. In some embodiments, the analysis of the ECG reveals ventricular fibrillation having a certain VF frequency F1, which corresponds to a period P1. In some embodiments, the inter-pulse time duration P2 is determined from the certain VF frequency F1. In some of those embodiments, the inter-pulse time duration P2 is determined so that it is within a factor of two of period P1. In some instances, the inter-pulse time duration P2 is determined so that it is substantially equal to period P1. The analysis generates a value 427 from P1, or F1, which is passed for generating the value of inter-pulse time duration P2.

VF frequency F2 can be measured in a number of ways. For example there can be counting of how frequently a threshold is crossed. Or a version of a Fourier transform can be performed, such as a Fast Fourier Transform (FFT). In some instances, the peak VF frequency can be estimated. To limit the computational power required to find the peak VF frequency, the FFT could be performed on a relatively short segment of data, perhaps only one or two seconds, and the FFT butterflies would only need to be calculated for frequencies in the normal VF range, which is about 5-10 Hz.

In FIG. 4, pacing pulses 451, . . . are shown as having the same spacing among them, which is the pacing rate. A good rate would be 300 bpm (beats per minute), for a VF with an average frequency of 5 Hz.

The above embodiments are not limiting for practicing embodiments of the invention. For example, the spacing of pacing pulses 451, . . . could vary. One variation is for the spacing to be a ramp—pacing could start at a relatively slow rate, and increase in an effort to achieve capture. In yet other embodiments, the spacing of these pacing pulses can be independent of the VF rate.

Further, while only four pacing pulses 451, 452, 453, 454 are shown, embodiments of the invention could be practiced with fewer, or more. Ten pulses may be a good value to achieve overdrive capture. As to a maximum number of pacing pulses, at some point it may be unhealthy for the patient to be paced at such a high rate for a long time, but if such pacing went on for only a few seconds there is probably no harm. For example, such pacing for, say 5 seconds, could represent as many as 500 pacing pulses—way more than necessary, but probably still no harm to the patient.

If the therapy fails to stop the fibrillation, it may be beneficial to try a different therapy. If defibrillation shock 448 was already delivered at the maximum energy available, then changing the pacing portion 450 of therapy 111 may be the only viable alternative. This is particularly true if multiple shocks have failed—why not try something else? The pacing therapy can be changed by varying the pacing rate, and possibly the number of pacing pulses, also known as the pulse train length. For example, there could be no pulses the first time; if there is failure, the pulse train length could increase in the next try, and then again after another failure. Moreover, the pulse rain magnitude could be varied depending on the patient impedance, selected defibrillation energy setting, and previous shock failure. It is also possible that switching to a defibrillation shock alone may prove beneficial as a backup.

In addition, all of what is written in this document about treating VF can also be used for treating other cardiac arrhythmias, such as shockable Ventricular Tachycardia ("VT"). Such could be performed with a synchronized cardio-version shock, followed by the same sequence of APSAT pulses.

The anti-tachy pacing pulses could be delivered from the same capacitor that stored the defibrillator energy, or could be delivered from another power source. If the defibrillator capacitor is used for pacing, the capacitor could be either pre-charged with enough energy for both defibrillation and pacing, or it could be recharged during the pacing process. The defibrillator discharge circuit 355, if implemented as an H-bridge, could be used as part of the pacing current path or the current source could be separate.

In some embodiments, measurement circuit 320 measures an impedance of the patient, while defibrillation shock 448 is being delivered. In such embodiments, capacitor 352 can be charged for delivering the additional pacing pulse to a value determined from the measured impedance.

Indeed, another advantage to this new external therapy is that the patient impedance value that is measured during defibrillation shock 448 may be utilized during pacing. To-date, defibrillators must charge the capacitor to a relatively high voltage, in order to deliver the desired current to the highest possible impedance that might be encountered. Pacing impedances can vary from 10 s of Ohms to ~2000 ohms, requiring a charge voltage of 300-400V in order to be able to reliably deliver 200 mA. With this new therapy, the patient impedance will be known before the pacing. Accordingly, capacitor 352 could be charged only as high as is necessary for this particular patient. Since most patients have a post-shock impedance of 200 ohms or less, 200 mA could be delivered with the capacitor being charged to a voltage of only about 40V. This low voltage requirement allows the pacing circuitry to be physically smaller, have lower cost, and consume less power than conventional external pacing circuitry.

Knowing the patient impedance also allows the circuit topology to be simplified. Conventional pacing circuitry requires a current source output to deliver the desired amount of current. This usually requires a method of delivering current, a method of sensing the amount of current flow, and feedback to control the current to the desired level. In accordance with embodiments of the invention, the APSAT pacing pulses may be delivered with a simpler arrangement. Because the patient impedance is known before the APSAT pacing pulses start, the current may be controlled simply by charging capacitor 352 to the desired voltage. For example, if it were desired to deliver 200 mA to an 80 ohm patient, the capacitor would be charged to 16V.

There are several ways in which defibrillator 300 can be designed according to embodiments of the invention. One way is to use the voltage remaining from defibrillation shock 448 for some or all the group 450 of pacing pulses. This may avoid or reduce the need to recharge before pacing. While a conventional defibrillator may choose to discharge the remaining capacitor voltage after a defibrillation shock (such as for safety reasons), a defibrillator delivering this new therapy may choose to retain that voltage for pacing, and perhaps discharge after the pacing.

The functions of this description may be implemented by one or more devices that include logic circuitry. The device performs functions and/or methods as are described in this document. The logic circuitry may include a processor that may be programmable for a general purpose, or dedicated, such as microcontroller, a microprocessor, a Digital Signal Processor (DSP), etc. For example, the device may be a digital computer like device, such as a general-purpose computer selectively activated or reconfigured by a computer program stored in the computer. Alternately, the device may be implemented by an Application Specific Integrated Circuit (ASIC), etc.

Moreover, methods are described below. The methods and algorithms presented herein are not necessarily inherently associated with any particular computer or other apparatus. Rather, various general-purpose machines may be used with programs in accordance with the teachings herein, or it may prove more convenient to construct more specialized apparatus to perform the required method steps. The required structure for a variety of these machines will become apparent from this description.

In all cases there should be borne in mind the distinction between methods in this description, and the method of operating a computing machine. This description relates both to methods in general, and also to steps for operating a computer and for processing electrical or other physical signals to generate other desired physical signals.

Programs are additionally included in this description, as are methods of operation of the programs. A program is generally defined as a group of steps leading to a desired result, due to their nature and their sequence. A program is usually advantageously implemented as a program for a computing machine, such as a general-purpose computer, a special purpose computer, a microprocessor, etc.

Storage media are additionally included in this description. Such media, individually or in combination with others, have stored thereon instructions of a program made according to embodiments of the invention. A storage medium according to embodiments of the invention is a computer-readable medium, such as a memory, and is read by the computing machine mentioned above.

Performing the steps or instructions of a program requires physical manipulations of physical quantities. Usually, though not necessarily, these quantities may be transferred, combined, compared, and otherwise manipulated or processed according to the instructions, and they may also be stored in a computer-readable medium. These quantities include, for example electrical, magnetic, and electromagnetic signals, and also states of matter that can be queried by such signals. It is convenient at times, principally for reasons of common usage, to refer to these quantities as bits, data bits, samples, values, symbols, characters, images, terms, numbers, or the like. It should be borne in mind, however, that all of these and similar terms are associated with the appropriate physical quantities, and that these terms are merely convenient labels applied to these physical quantities, individually or in groups.

This detailed description is presented largely in terms of flowcharts, display images, algorithms, and symbolic representations of operations of data bits within at least one computer readable medium, such as a memory. Indeed, such descriptions and representations are the type of convenient labels used by those skilled in programming and/or the data processing arts to effectively convey the substance of their work to others skilled in the art. A person skilled in the art of programming may use these descriptions to readily generate specific instructions for implementing a program according to embodiments of the invention.

Often, for the sake of convenience only, it is preferred to implement and describe a program as various interconnected distinct software modules or features, individually and collectively also known as software. This is not necessary, however, and there may be cases where modules are equivalently aggregated into a single program with unclear boundaries. In any event, the software modules or features of this description may be implemented by themselves, or in combination with others. Even though it is said that the program may be stored in a computer-readable medium, it should be clear to a person skilled in the art that it need not be a single memory, or even a single machine. Various portions, modules or features of it may reside in separate memories, or even separate machines. The separate machines may be connected directly, or through a network, such as a local access network (LAN), or a global network, such as the Internet.

It will be appreciated that some of these methods may include software steps that may be performed by different modules of an overall software architecture. For example, data forwarding in a router may be performed in a data plane, which consults a local routing table. Collection of performance data may also be performed in a data plane. The performance data may be processed in a control plane, which accordingly may update the local routing table, in addition to neighboring ones. A person skilled in the art will discern which step is best performed in which plane.

An economy is achieved in the present document in that a single set of flowcharts is used to describe both programs, and also methods. So, while flowcharts are described in terms of boxes, they can mean both method and programs.

For this description, the methods may be implemented by machine operations. In other words, embodiments of programs are made such that they perform methods in accordance to embodiments of the invention that are described in this document. These may be optionally performed in conjunction with one or more human operators performing some, but not all of them. As per the above, the users need not be collocated with each other, but each only with a machine that houses a portion of the program. Alternately, some of these machines may operate automatically, without users and/or independently from each other.

Example Methods

Figure 5:
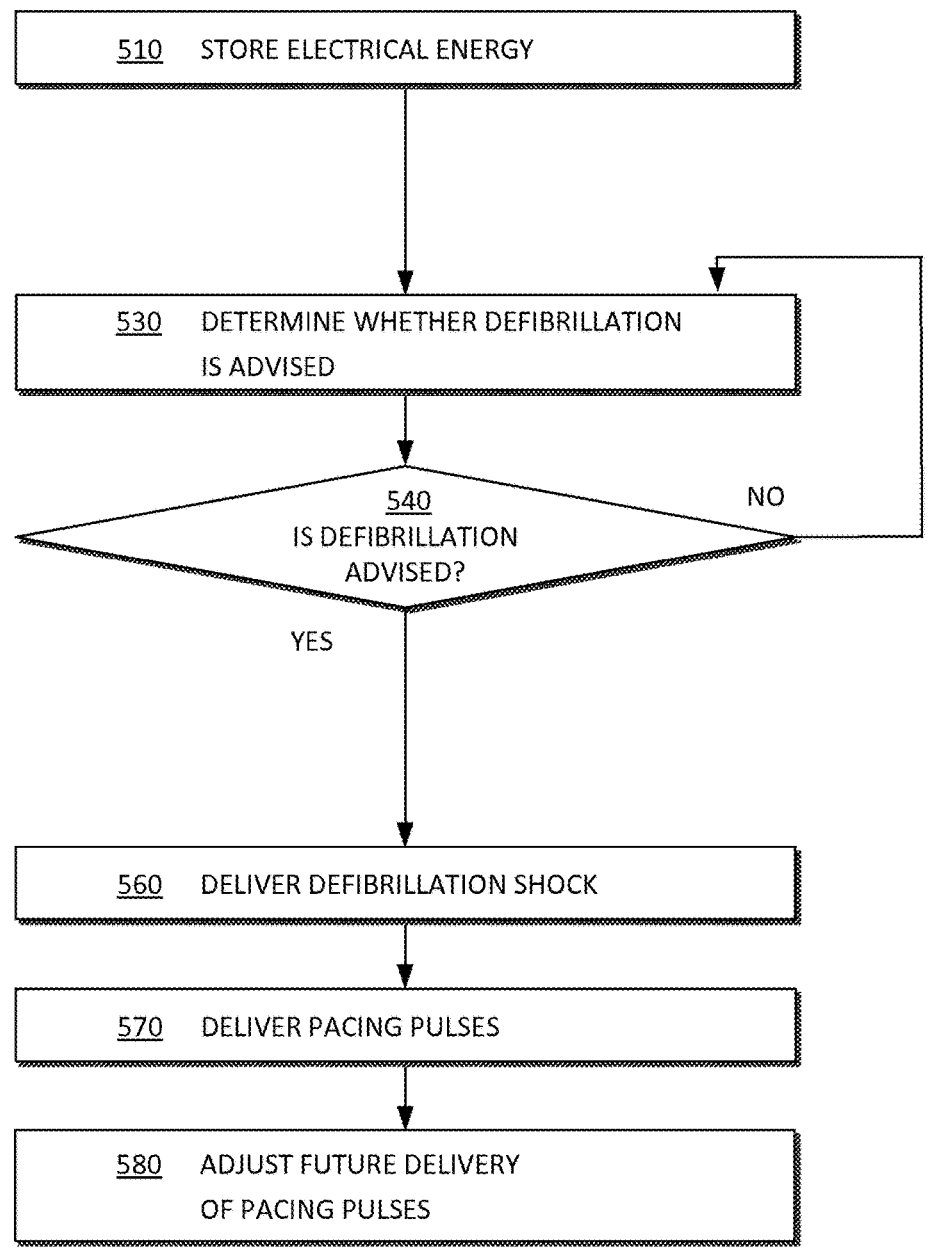
FIG. 5 is a flowchart for illustrating methods according to embodiments.

FIG. 5 shows a flowchart 500 for describing methods according to embodiments, for an external medical device to deliver electrical therapy to a patient. The method of flowchart 500 may also be practiced by external defibrillators made according to embodiments described above, such as defibrillator 300.

According to an operation 510, electrical energy is stored, such as in an energy storage module.

According to a next operation 530, it is determined whether defibrillation is advised for the patient.

According to a next operation 540, execution branches according to the outcome of operation 530. If defibrillation is not advised, execution can return to operation 530 as shown in the example of FIG. 5, or terminate.

According to a next operation 560, if defibrillation is indeed advised at operation 540, a defibrillation shock is delivered to the patient. As also per the above, the defibrillation shock can be delivered automatically or responsive to a user operating a user interface of the device.

According to a next operation 570, pacing pulses are delivered to the patient, such as shown in FIG. 4. Again as per the above, in some embodiments, the pacing pulses can be delivered without further analyzing an ECG of the patient, and/or without making any other preparation or needing to receive any input for operation 570 after operation 560.

According to an optional next operation 580, a future delivery of pacing pulses is adjusted. Operation 580 can be performed in a number of ways, and in a number of different contexts.

In one context, the therapy will be repeated, but with different parameters. For example, an adjustment can be made in how the inter-pulse time duration is determined, or the spacing of the pacing pulses, or their number or their amplitude.

Another context is when the defibrillation shock and one or more of the pacing pulses have been delivered to the patient as a test for gauging a patient's reaction. The test would be for preparing for a defibrillator precustomized to the patient, such as a wearable defibrillator or a defibrillator for use in a facility like a hospital or special care unit or a retirement home. It is possible that some patients may find that post-shock pacing may be arrhythmogenic, while others may find it to be anti-arrhythmic. If post-shock pacing is known to be harmful to a particular patient, then it may be desirable to configure the device to deliver a shock alone for that patient. Accordingly, the future delivery of the pacing pulses can be adjusted in any number of ways. In some embodiments, the pacing pulses may not be delivered at all. For patients that shouldn't receive pacing pulses, the determination would have to occur at 570, not at 580 where the pacing pulses are adjusted.

Figure 6:
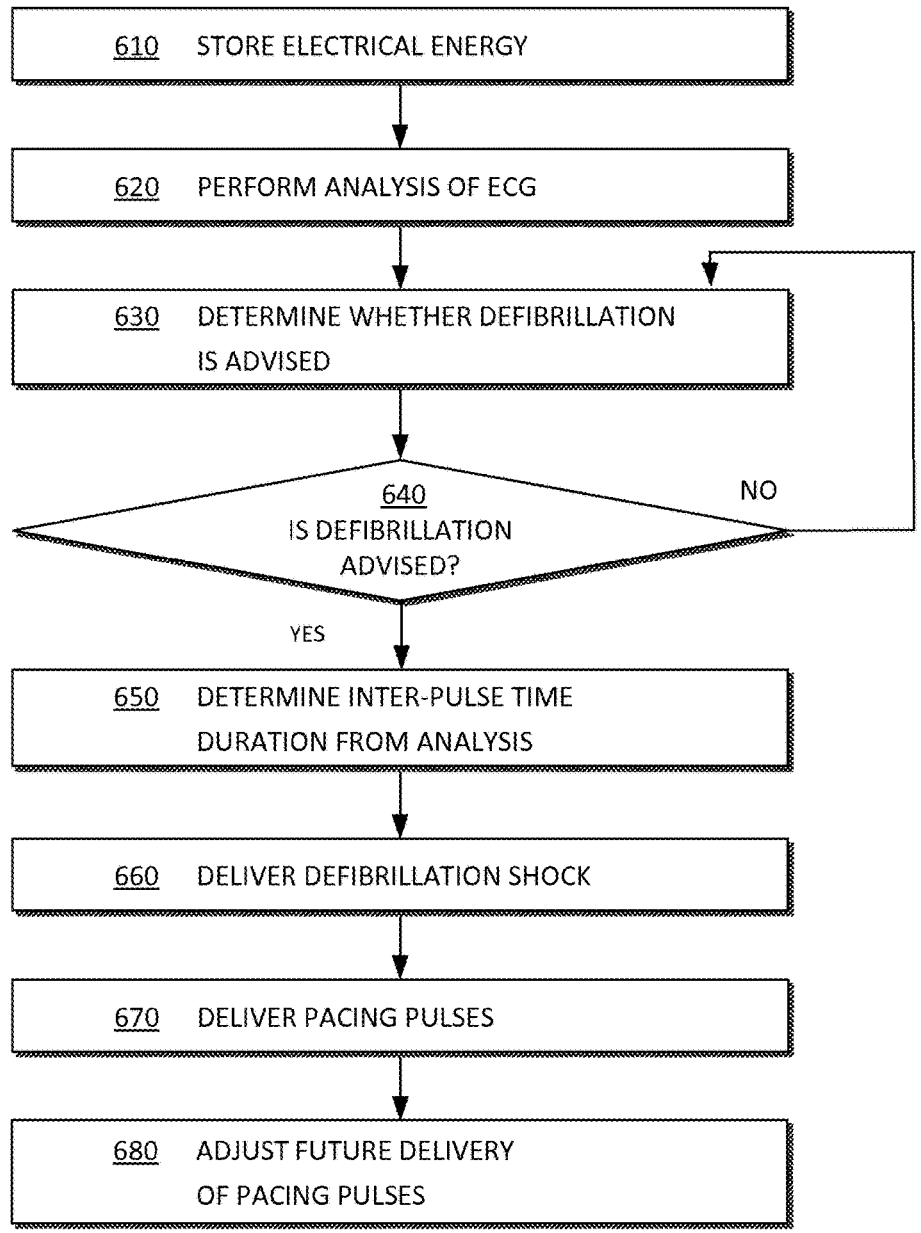
FIG. 6 is a flowchart for illustrating additional methods according to embodiments.

FIG. 6 shows a flowchart 600 for describing methods according to embodiments for an external medical device to deliver electrical therapy to a patient. The method of flowchart 600 may also be practiced by external defibrillators made according to embodiments described above, such as defibrillator 300. It will be recognized that a number of the operations of flowchart 600 are similar to those of flowchart 500.

According to an operation 610, electrical energy is stored in a battery of the device, for example when the device is initially prepared for use. According to a next operation 620, an ECG of the patient is analyzed.

According to a next operation 630, it is determined whether defibrillation is advised for the patient. Operation 630 can be performed as a result of the analysis of the ECG at operation 620.

According to a next operation 640, execution branches according to the outcome of operation 630. If defibrillation is not advised, execution can return to operation 630 as shown in the example of FIG. 6, or terminate.

According to a next operation 650, an inter-pulse time duration is determined from the ECG analysis of operation 620.

According to a next operation 660, if defibrillation is indeed advised at operation 640, a defibrillation shock is delivered to the patient. As also per the above, the defibrillation shock can be delivered automatically or responsive to a user operating a user interface of the device. For delivering a shock, the stored energy would be used to charge the capacitor. In most embodiments, the capacitor would be charged only after it has been determined that shock is advised.

According to an optional next operation 670, pacing pulses are delivered to the patient. Two successive pacing pulses may have a spacing of the inter-pulse time duration. Again as per the above, in some embodiments, the pacing pulses can be delivered without further analyzing an ECG of the patient, and/or without making any other preparation or needing to receive any input for operation 670 after operation 660.

According to an optional next operation 680, a future delivery of pacing pulses is adjusted. Operation 680 can be performed similarly to previously described operation 580.

For both flowcharts 500 and 600, it will be recognized that a number of their operations can be augmented with what was described above.

In accordance with embodiments of the invention, the pacing is far different from the pacing therapy typically delivered from an external defibrillator/pacer. Typical anti-bradycardia pacing is done at a rate of 80-90 bpm, and is inhibited when an intrinsic complex is detected. In accordance with embodiments of the invention, the pacing is delivered after defibrillation shock 448, at a higher rate, such as 300 bpm. In other words, the spacing between pulses 452, 453 can be such that these two successive pacing pulses are delivered faster than an instantaneous rate of 200 bpm. Moreover, in accordance with embodiments of the invention, pacing pulses 452, 453 are not inhibited by complexes detected in the ECG.

Pacing for anti-bradycardia is different. More particularly, ECG sensing is required, plus the determination of whether QRS complexes are present. If there is a period of time with no QRS complexes, the defibrillator delivers a pacing pulse. This requires ECG sensing electrodes that are separate from the therapy electrodes because the artifact created by the pacing pulse prohibits therapy and sensing from the same set of electrodes. There are currently no AEDs that are able to pace because AEDs have only one set of electrodes. In accordance with embodiments of the invention, the pacing, however, APSAT pacing could be delivered from an AED or a manual defibrillator, because it does not necessarily require a separate set of sensing electrodes.

Still on the topic of pacing for anti-bradycardia, the delivery of conventional anti-bradycardia pacing is also complicated because it is difficult to know whether the patient is conscious when the pacing pulses are delivered. If the patient is conscious, then steps must be taken to alleviate the pain. Typically, the current is set to the minimum level in order to achieve capture. Still, sedation may be necessary.

Notes and Additional/Alternative Implementation Details

In the above description of exemplary implementations, for purposes of explanation, specific numbers, materials configurations, and other details are set forth in order to better explain the present invention, as claimed. However, it will be apparent to one skilled in the art that the claimed invention may be practiced using different details than the exemplary ones described herein. In other instances, well-known features are omitted or simplified to clarify the description of the exemplary implementations.

The inventor intends the described exemplary implementations to be primarily examples. The inventor does not intend these exemplary implementations to limit the scope of the appended claims. Rather, the inventor has contemplated that the claimed invention might also be embodied and implemented in other ways, in conjunction with other present or future technologies.

Moreover, the word "exemplary" is used herein to mean serving as an example, instance, or illustration. Any aspect or design described herein as exemplary is not necessarily to be construed as preferred or advantageous over other aspects or designs. Rather, use of the word "exemplary" is intended to present concepts and techniques in a concrete fashion. The term "technology," for instance, may refer to one or more devices, apparatuses, systems, methods, articles of manufacture, and/or computer-readable instructions as indicated by the context described herein.

As used in this application, the term "or" is intended to mean an inclusive "or" rather than an exclusive "or." That is, unless specified otherwise or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more," unless specified otherwise or clear from context to be directed to a singular form.

Note that the order in which the processes are described is not intended to be construed as a limitation, and any number of the described process blocks can be combined in any order to implement the processes or an alternate process. Additionally, individual blocks may be deleted from the processes without departing from the spirit and scope of the subject matter described herein.

One or more embodiments described herein may be implemented fully or partially in software and/or firmware. This software and/or firmware may take the form of instructions contained in or on a non-transitory computer-readable storage medium. Those instructions may then be read and executed by one or more processors to enable performance of the operations described herein. The instructions may be in any suitable form, such as but not limited to source code, compiled code, interpreted code, executable code, static code, dynamic code, and the like. Such a computer-readable medium may include any tangible non-transitory medium for storing information in a form readable by one or more computers, such as but not limited to read only memory (ROM); random access memory (RAM); magnetic disk storage media; optical storage media; a flash memory, etc.

The term "computer-readable media" includes computer-storage media. For example, computer-storage media may include, but are not limited to, magnetic storage devices (e.g., hard disk, floppy disk, and magnetic strips), optical disks (e.g., compact disk [CD] and digital versatile disk [DVD]), smart cards, flash memory devices (e.g., thumb drive, stick, key drive, and SD cards), and volatile and nonvolatile memory (e.g., RAM and ROM).

In the claims appended herein, the inventor invokes 35 U.S.C. § 112, paragraph 6 only when the words "means for" or "steps for" are used in the claim. If such words are not used in a claim, then the inventor does not intend for the claim to be construed to cover the corresponding structure, material, or acts described herein (and equivalents thereof) in accordance with 35 U.S.C. § 112, paragraph 6.

What is claimed is:

1. An external medical device that facilitates delivery of electrical energy to a patient, the external medical device comprising:
a housing external to the patient;
an energy storage module within the housing, the energy storage module configured to store electrical energy;
a processor configured to determine whether defibrillation is advised for the patient by performing an analysis of an ECG of the patient and, if so, the processor being further configured to control a delivery of the stored electrical energy to the patient, the delivery being controlled so that:
a first portion of the stored electrical energy is delivered as a defibrillation shock that has an energy level of at least 50 J, and
a second portion of the stored electrical energy is delivered after the defibrillation shock as one or more pacing pulses, at least one of the one or more pacing pulses having an energy of at most 4.8 J, an energy of at least one of the one or more pacing pulses being based upon the performed analysis of the ECG of the patient.

2. The external medical device of claim 1, in which the external medical device is one of a monitor-defibrillator, an AED and a wearable cardiac defibrillator.

3. The external medical device of claim 1, in which the processor is further configured to automatically control delivery of the stored electrical energy if the processor determines that defibrillation is advised for the patient.

4. The external medical device of claim 1, further comprising:
a user interface, and
in which the processor is further configured to deliver the stored electrical energy in response to an input received at the user interface.

5. The external medical device of claim 1, in which the first one of the pacing pulses is delivered within five seconds after the defibrillation shock is delivered.

6. The external medical device of claim 1, in which the first one of the pacing pulses is delivered automatically after the first portion of the stored electrical energy has been delivered and without any further analysis of an ECG of the patient after the defibrillation shock has been delivered.

7. An external medical device that facilitates delivery of electrical energy to a patient, the external medical device comprising:
a housing external to the patient;
an energy storage module within the housing, the energy storage module configured to store electrical energy;
a processor configured to determine whether defibrillation is advised for the patient by performing an analysis of an ECG of the patient and, if so, the processor being further configured to control a delivery of the stored electrical energy to the patient, the delivery being controlled so that:
a first portion of the stored electrical energy is delivered as a defibrillation shock that has an energy level of at least 50 J, and
a second portion of the stored electrical energy is delivered after the defibrillation shock as a sequence of two or more pacing pulses, at least one of the two or more pacing pulses having an energy of at most 4.8 J, an inter-pulse time duration between two successive ones of the two or more pacing pulses being based upon the performed analysis of the ECG of the patient.

8. The external medical device of claim 7, in which the external medical device is one of a monitor-defibrillator, an AED and a wearable cardiac defibrillator.

9. The external medical device of claim 7, in which the processor is further configured to automatically control delivery of the stored electrical energy if the processor determines that defibrillation is advised for the patient.

10. The external medical device of claim 7, further comprising:
a user interface, and
in which the processor is further configured to deliver the stored electrical energy in response to an input received at the user interface.

11. The external medical device of claim 7, in which the first one of the pacing pulses is delivered within five seconds after the defibrillation shock is delivered.

12. The external medical device of claim 7, in which the first one of the pacing pulses is delivered automatically after the first portion of the stored electrical energy has been delivered and without any further analysis of an ECG of the patient after the defibrillation shock has been delivered.

13. The external medical device of claim 7, in which the analysis has revealed ventricular fibrillation having a certain VF frequency, and the inter-pulse time duration is determined from the certain VF frequency.

14. An external medical device that facilitates delivery of electrical energy to a patient, the external medical device comprising:
a housing external to the patient;
an energy storage module within the housing, the energy storage module configured to store electrical energy;
a processor configured to determine whether defibrillation is advised for the patient by performing an analysis of an ECG of the patient and, if so, the processor being further configured to control a delivery of the stored electrical energy to the patient, the delivery being controlled so that:
a first portion of the stored electrical energy is delivered as a defibrillation shock that has an energy level of at least 50 J, and
a second portion of the stored electrical energy is delivered after the defibrillation shock as one or more pacing pulses, the first one of the one or more pacing pulses being delivered automatically after the first portion of the stored electrical energy has been delivered and without any further analysis of an ECG of the patient after the first portion of the stored electrical energy has been delivered.

15. The external medical device of claim 14, in which an energy of at least one of the one or more pacing pulses is based upon the analysis of the ECG of the patient that was performed prior to the first portion of the stored electrical energy being delivered.

16. The external medical device of claim 14, in which the external medical device is one of a monitor-defibrillator, an AED and a wearable cardiac defibrillator.

17. The external medical device of claim 14, in which the processor is further configured to automatically control delivery of the stored electrical energy if the processor determines that defibrillation is advised for the patient.

18. The external medical device of claim 14, further comprising:

a user interface, and in which the processor is further configured to deliver the stored electrical energy in response to an input received at the user interface.

19. The external medical device of claim 14, in which the first one of the pacing pulses is delivered within five seconds after the defibrillation shock is delivered.

20. The external medical device of claim 14, in which the second portion of the stored electrical energy is delivered as two or more pacing pulses, and an inter-pulse time duration between two successive ones of the two or more pacing pulses is based upon the performed analysis of the ECG of the patient.

21. The external medical device of claim 14, in which the second portion of the stored electrical energy is delivered as two or more pacing pulses, and the analysis has revealed ventricular fibrillation having a certain VF frequency, and an inter-pulse time duration between two successive ones of the two or more pacing pulses is determined from the certain VF frequency.

\* \* \* \* \*

UNITED STATES PATENT AND TRADEMARK OFFICE
CERTIFICATE OF CORRECTION

PATENT NO. : 9,889,313 B2
APPLICATION NO. : 15/430470
DATED : February 13, 2018
INVENTOR(S) : Sullivan et al.

Page 1 of 1

It is certified that error appears in the above-identified patent and that said Letters Patent is hereby corrected as shown below:

In Column 2, Line 8, Delete "arrythmias" and insert -- arrhythmias --, therefor.

Signed and Sealed this
Twentieth Day of November, 2018

Andrei Iancu
*Director of the United States Patent and Trademark Office*